United States Patent [19]

Coe et al.

[11] Patent Number: 5,536,722
[45] Date of Patent: Jul. 16, 1996

[54] TRIAZINE DERIVATIVES FOR ENHANCING ANTITUMOR ACTIVITY

[75] Inventors: Jotham W. Coe, Mystic; Anton F. J. Fliri, Norwich; Takushi Kaneko, Guilford; Eric R. Larson, Mystic, all of Conn.

[73] Assignee: Pfizer Inc., New York, N.Y.

[21] Appl. No.: 232,083

[22] PCT Filed: Sep. 16, 1992

[86] PCT No.: PCT/US92/07656

§ 371 Date: May 11, 1994

§ 102(e) Date: May 11, 1994

[87] PCT Pub. No.: WO93/10116

PCT Pub. Date: May 27, 1993

Related U.S. Application Data

[63] Continuation of Ser. No. 790,789, Nov. 12, 1991, abandoned.

[51] Int. Cl.$^6$ ............... C07D 251/70; C07D 403/04; A61K 31/53
[52] U.S. Cl. ............................. 514/245; 544/198
[58] Field of Search .................. 544/198; 514/245

[56] References Cited

U.S. PATENT DOCUMENTS 4,514,398   4/1985   Regnier et al. .................. 514/245

FOREIGN PATENT DOCUMENTS

| | | |
|---|---|---|
| 0466586 | 1/1992 | European Pat. Off. . |
| 0502788 | 9/1992 | European Pat. Off. . |
| 2660558 | 10/1991 | France . |
| 9207844 | 5/1992 | WIPO . |

OTHER PUBLICATIONS

D. Boesch et al., Cancer Research, 51, 4226–4233, Aug. 15, 1991.
Twentyman et al., Cancer Chemotherapy and Pharmacology (1991) 29: 24–28.
Sato et al., Cancer Research 51, 2420–2424, May 1, 1991.
T. Tsuruo, Xenobiotics and Cancer, L. Ernster et al. (Eds.), Japan Sci. Soc. Press, Tokyo/Taylor & Francis Ltd., London, pp. 241–251, 1991.
Fojo et al., Cancer Research, 45, 3002–3007, Jun. 1985.
T. Kaneko, Current Opinion in Therapeutic Patents, Jul. 1991.
D. Hochhauser and A. L. Harris, Brit. Med. Bull., 47, 178–190 (1991).
W. T. Bellamy, W. S. Dalton and R. T. Dorr, Cancer Invest., 8, 547–562 (1990).
Gottesman et al., J. Biol. Chem., vol. 263, No. 25, pp. 12163–12166, 1988.

*Primary Examiner*—John M. Ford
*Attorney, Agent, or Firm*—Peter C. Richardson; Gregg C. Benson; John D. Conway

[57] ABSTRACT

2,4,6-Triaminotriazine derivatives as potentiators of chemotherapeutic agents in the treatment of cancer.

14 Claims, No Drawings

TRIAZINE DERIVATIVES FOR ENHANCING ANTITUMOR ACTIVITY

Cross Reference to Related Applications

This application is the national stage of International Application No. PCT/US92/07656, filed Sep. 16, 1992, designating, inter alia, the United States which is a continuation of U.S. application Ser. No. 07/790,789, filed Nov. 12, 1991, now abandoned.

BACKGROUND OF THE INVENTION

This invention relates to 2,4,6 triaminotriazines and their use as sensitizers of tumor cells to anticancer agents.

In cancer chemotherapy the effectiveness of anticancer drugs is often limited by the resistance of tumor cells. Some tumors such as of the colon, pancreas, kidney and liver are generally innately resistant, and other responding tumors often develop resistance during the course of chemotherapy. The phenomena of multidrug resistance (MDR) is characterized by the tumor cell's cross-resistance to target of resistance include adriamycin, daunomycin, vinblastine, vincristine, daxol, actinomycin D and etoposide. The resistance cells are often associated with overexpression of the mdrl gene. This gene product is a family of 140–220 kd trans-membrane phosphoglycoprotein (P-glycoprotein) which functions as an ATP-dependent efflux pump. Thus, it has been postulated that this efflux mechanism keeps the intracellular level of the anticancer drug low, allowing the tumor cells to survive.

In recent years various substances such as verapamil, nifedipine and diltiazem have been used in vitro experimental systems to reverse the MDR phenomena. More recently some of these agents have been tested clinically as MDR reversing agents. Little efficacy has been observed with verapamil or trifluoroperazine. Thus, there is a need for an effective MDR reversing agent.

2,4,6-Triamino-1,3,5-triazines are reported to be useful in the treatment of tissue hypoxia in European Patent Application 90733A.

SUMMARY OF THE INVENTION

The compounds of the present invention are of the formula

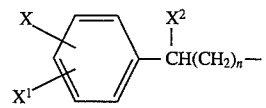

I and the pharmaceutically acceptable acid addition salts thereof wherein $R_1$ and $R_2$ are taken with the nitrogen atom to which they are attached and form a moiety of the formula

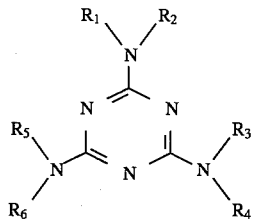

where $R_7$ is hydrogen, alkyl of one to three carbon atoms or dialkoxyphenylalkyl said alkoxy each of one to three carbon atoms and said alkyl of one to three carbon atoms, Q and $Q^1$ are each hydrogen, alkyl of one to three carbon atoms, alkoxy of one to three carbon atoms, fluoro, bromo, iodo, chloro, trifluoromethyl, amino, alkylamino having one to three carbon atoms or dialkylamino having two to six carbon atoms and Q and $Q^1$ taken together are methylenedioxy or ethylenedioxy; $R_3$ is hydrogen, or alkyl of one to three carbon atoms, $R_4$ is (a) hydrogen, (b) alkyl of one to three carbon atoms, (c) aralkyl of the formula

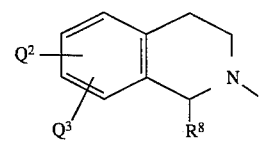

where X and $X^1$ are each hydrogen, alkyl of one to three carbon atoms, hydroxy, alkoxy of one to three carbon atoms, fluoro, chloro, bromo, iodo, trifluoromethyl, amino, alkylamino of one to three carbon atoms or dialkylamino of two to six carbon atoms, X and $X^1$ taken together are methylenedioxy or ethylenedioxy, n is an integer of 0 to 1 and $X^2$ is hydrogen, alkoxy of one to three carbon atoms or hydroxy or (d) aralkyl of the formula

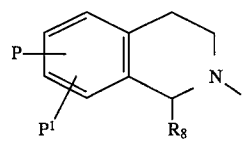

where Z and $Z^1$ are each hydrogen, alkyl of one to three carbon atoms, hydroxy, alkoxy of one to three carbon atoms, fluoro, chloro, bromo, iodo, trifluoromethyl, amino, alkylamino of one to three carbon atoms or dialkylamino of two to six carbon atoms, Z and $Z^1$ taken together are methylenedioxy or ethylenedioxy, m is an integer of 0 or 1, W is O,S or a chemical bond and A is alkylene of two to four carbon atoms and $R_3$ and $R_4$ when taken together with the nitrogen to which they are attached to form a moiety of the formula

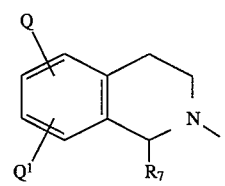

where P and $P^1$ are each hydrogen, alkyl of one to three carbon atoms, alkoxy of one to three carbon atoms, fluoro, bromo, iodo, chloro, amino, alkylamino of one to three carbon atoms or dialkylamino of two to six carbon atoms, P and $P^1$ taken together are methylenedioxy or ethylenedioxy and $R_8$ is hydrogen, alkyl of one to three carbon atoms or dialkoxyphenylalkyl said alkoxy each of one to three carbon atoms and said alkyl of one to three carbon atoms; $R_5$ is (a) hydrogen, (b) alkyl of one to three carbon atoms, (c) benzodioxan-2-ylmethyl, (d) aralkyl of the formula

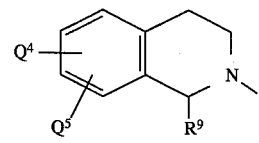

where Y and $Y^1$ are each hydrogen, alkyl of one to three carbon atoms, hydroxy, alkoxy of one to three carbon atoms, fluoro, chloro, bromo, iodo, trifluoromethyl, alkylamino of one to three carbon atoms or dialkylamino of two to six carbon atoms, Y and $Y^1$ taken together are methylenedioxy or ethylenedioxy, p is an integer of 0 or 1 and $Y^2$ is hydrogen, hydroxy or alkoxy of one to three carbon atoms or (e) aralkyl of the formula

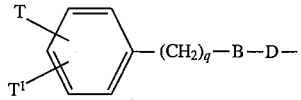

where T and $T^1$ are each hydrogen, alkyl of one to three carbon atoms, hydroxy, alkoxy of one to three carbon atoms, fluoro, chloro, bromo, iodo, trifluoromethyl, amino, alkylamino of one to three carbon atoms or dialkylamino of two to six carbon atoms, T and $T^1$ taken together are methylenedioxy or ethylenedioxy, g is an integer of 0 or 1, B is O,S or a chemical bond and D is alkylene of two to four carbon atoms, $R_6$ is hydrogen or alkyl of one to three carbon atoms and $R_5$ and $R_6$ when taken together with the nitrogen to which they are attached form a moiety of the formula

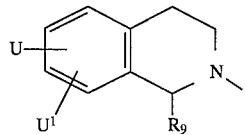

where U and $U^1$ are each hydrogen, alkyl of one to three carbon atoms, alkoxy of one to three carbon atoms, fluoro, bromo, iodo, chloro, trifluoromethyl, amino, alkylamino of one to three carbon atoms or dialkylamino of two to six carbon atoms, U and $U^1$ taken together are methylenedioxy or ethylenedioxy and $R_9$ is hydrogen, alkyl of one to three carbon atoms or dialkoxyphenylalkyl said alkoxy each of one to three carbon atoms and said alkyl of one to three carbon atoms with the proviso that when $X^2$ is hydroxy or said alkoxy then n is 1 and when $Y^2$ is hydroxy or said alkoxy then p is 1.

A preferred group of compounds are those where $R_1$ and $R_2$ when taken together with the nitrogen to which they are attached form a moiety

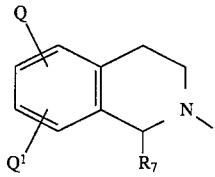

where Q is 6-methoxy, $Q^1$ is 7-methoxy and $R_7$ is hydrogen or dialkoxyphenylalkyl said alkoxy each of one to three carbon atoms and said alkyl of one to three carbon atoms; $R_3$ and $R_4$ when taken together with the nitrogen to which they are attached form a moiety of the formula

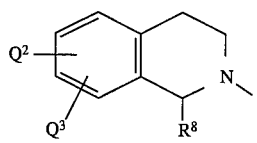

where P is 6-methoxy, $P^1$ is 7-methoxy and $R_8$ is hydrogen; and $R_5$ is hydrogen, benzodioxan-2-ylmethyl or aralkyl of the formula

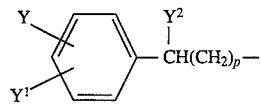

where Y and $Y^1$ are each alkoxy of one to three carbon atoms, $Y^2$ is hydrogen and p is 1. Especially preferred within this group are the compounds where $R_7$ is hydrogen, $R_5$ is aralkyl of the formula

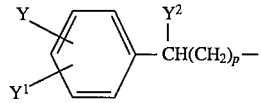

where Y is 3-methoxy, $Y^1$ is 4-methoxy and $R_6$ is hydrogen, where $R_7$ is 3,4-dimethoxybenzyl, $R_5$ is benzodioxan-2-ylmethyl and $R_6$ is hydrogen and where $R_7$ is 3,4 dimethoxybenzyl, and $R^5$ and $R^6$ are each hydrogen.

A second preferred group of compounds are those where $R_1$ and $R_2$ when taken together with the nitrogen to which they are attached form a moiety of the formula

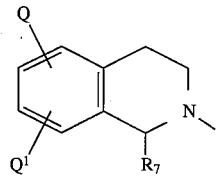

where Q is 6-methoxy, $Q^1$ is 7-methoxy, and $R_7$ is hydrogen or dialkoxyphenylalkyl said alkyl each of one to three carbon atoms and said alkyl of one to three carbon atoms; $R_3$ is hydrogen and $R_4$ is aralkyl of the formula

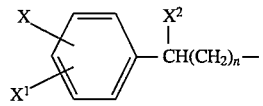

where n is 1; and $R_5$ is aralkyl of the formula

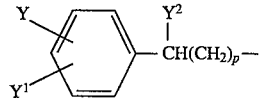

where p is 1 and $Y^2$ is hydrogen and $R_6$ is hydrogen. Especially preferred within this group are the compounds where $R_7$ is hydrogen X is 3-methoxy, $X^1$ is 4-methoxy, $X^2$ is hydrogen, Y is 3-methoxy and $Y^1$ is 4-methoxy, where $R_7$ is 3,4-dimethoxybenzyl, X is 3-methoxy, $X^1$ is 4-methoxy, $X^2$ is hydrogen, Y is 3-methoxy and $Y^1$ is 4-methoxy, where $R_7$ is hydrogen, X is 3-methoxy, $X^1$ is 4-methoxy, $X^2$ is methoxy, Y is 3-methoxy and $Y^1$ is 4-methoxy, where $R_7$ is hydrogen, X is hydrogen, $X^1$ is 4-amino, $X^2$ is hydrogen, Y is 3-methoxy and $Y^1$ is 4-methoxy, where $R_7$ is 3,4-dimethoxybenzyl, X is 3-methoxy, $X^1$ is 4-methoxy, Y is 3-methoxy, $Y^1$ is 4-methoxy, and where $R_7$ is 3,4-dimethoxybenzyl, X is hydrogen, $X^1$ is 4-amino, Y is 3-methoxy and $Y^1$ is 4-methoxy.

The present invention also includes a method of inhibiting a P-glycoprotein in a mammal in need of such treatment which comprises administering to said mammal a P-glycoprotein inhibiting amount of a compound of formula I. Preferred is the method where the mammal is a human suffering from cancer and said compound is administered before, with or after the administration to said human of an anticancer effective amount of a chemotherapeutic agent.

Also included is a pharmaceutical composition for administration to a mammal which comprises a P-glycoprotein inhibiting amount of a compound of formula I, a pharmaceutically acceptable carrier and, optionally, an anticancer effective amount of a chemotherapeutic agent.

As previously indicated, the compounds of formula I form pharmaceutically acceptable acid addition salts. Said pharmaceutically acceptable acid addition salts include, but are not limited to, those with HCl, HBr, $HNO_3$, $H_2SO_4$, $H_3PO_4$, $CH_3SO_3H$, $C_6H_5SO_3H$, $CH_3CO_2H$, gluconic acid, tartaric acid, maleic acid and succinic acid. In the case of those compounds of the formula (I) which contain a further basic nitrogen, it will, of course, be possible to from diacid addition salts (e.,g., the dihydrochloride) as well as the usual monoacid addition salt.

As one skilled in the art recognizes, compounds of formula I have the potential for containing asymmetric carbon atoms. All these potential isomers are considered within the scope of the present invention.

DETAILED DESCRIPTION OF THE INVENTION

Compounds of the present invention are prepared by the reaction of 2,4,6-trichloro-1,3,5-triazine (cyanuric chloride) with an equivalent of an appropriate amine, $R_1R_2NH$, followed by the reaction of the product, a 2,4-dichloro-6-amino-1,3,5-triazine derivative, with a second equivalent of appropriate amine, $R_3R_4NH$, followed by the reaction of the product, a 2-chloro-4,6-diamino-1,3,5-triazine with a third equivalent of an appropriate amine, $R_5R_6NH$.

In a more detailed description of the procedure one molar equivalent of cyanuric chloride and one molar equivalent of an amine, $R_1R_2NH$, and one molar equivalent of an inorganic base such as an alkali metal hydroxide or alkali metal bicarbonate dissolved in a minimum amount of water, are combined in a water miscible solvent, such as dioxane, dimethylacetamide or N-methyl-2-pyrrolidone, and maintained at 0°–100° C. for a period of 1 to 48 hours.

The product can be filtered or the reaction mixture can be quenched with water and the product either filtered or extracted with a water immiscible solvent such as methylene chloride or ethyl acetate. Separation of the extracting solvent and evaporation provides the product. Frequently the residual can be induced to crystallize by trituration with an organic-solvent,and further purified by recrystallization or column chromatography.

The isolated 2,4-dichloro-6-amino-1,3,5-triazine derivative can be further reacted with the second amine, $R_3R_4NH$, in a manner similar to that described for the reaction of cyanuric acid with $R_1R_2NH$. Isolation and purification of the product, a 2-chloro-4,6-diamino-1,3,5-triazine derivative, is essentially the same as previously described.

The isolated 2-chloro-4,6-diamino-1,3,5-triazine derivative is subsequently reacted with the amine $R_5R_6NH$ in a manner similar to that previously described for the reactions of $R_1R_2NH$ and $R_3R_4NH$ which the requisite chloro compounds. Isolation and purification are also carried out in a similar manner.

When the structure of I is such that any one of the amino substituents, $R_1R_2N$, $R_3R_4N$ or $R_5R_6N$ are the same, it is convenient to react the cyanuric chloride with two molar equivalents of the amine along which two molar equivalents of the inorganic base.

The products of the present invention can readily be converted to acid addition salts by adding the free base to an ethanolic solution of the appropriate acid. Further purification of the salt, if needed, can be carried out by recrystallization.

Generation of the free base from an acid addition salt can readily be carried out by treating an aqueous solution or suspension of the salt with at least one equivalent of an organic or inorganic base followed by extraction of the free base product with a water immiscible solvent such as ethyl acetate or methylene chloride. Removal of the solvent gives the desired base.

Compounds of formula I are inhibitors of the functions of P-glycoprotein, particularly human mdr 1 protein or P-glycoprotein related and membrane associate proteins which are participating in the transport of xenobiotics or proteins across membranes e.g., cell membranes of eukariotic and proeukariotic origin e.g., pmfdr, however not exclusive or restricted to these examples.

Compounds enclosed in general formula I are useful in combination chemotherapy of cancer, malaria, viral infections such as AIDS, in therapy of septic shock syndrome or inflammation and may be useful in enhancing of the xenobiotics limited due to the presence of P-glycoprotein or P-glycoprotein related functional proteins. Compounds of formula I increase the activity/efficacy of adrimycin, daunomycin, etoposide, epipodophyllotoxin congeners, actinomycin D, emetin, daxol, vincristine, vinblastine, chloroquine, antracycline antibiotics and of drugs which are structurally and functionally related to the above mentioned examples in particular when the activity of these drugs has been shown to be limited due to the presence and function of P-glycoprotein, e.g. human mdr 1 protein or P-glycoprotein related proteins.

The compounds of the present invention are evaluated as potentiators of chemotherapeutic agents using a Cellular Drug Retention Assay. This assay was designed to study the effect of compounds on cellular retention of radiolabeled drug. In this case 14C-adriamycin retention by multidrug resistant human carcinoma cells, KBV1, is measured.

KBV1 cells are routinely grown in tissue culture as monolayers in DMEM high glucose medium containing 1 ug/ml vinblastine, 10% heat inactivated fetal calf serum and supplemented with Glutamine, Pen-strep and Garamycin.

The assay protocol (described below) should be applicable with minor modifications, to a wide variety of cell lines grown in tissue culture.

Assay Protocol:

(1) Seed replicate 6-well tissue culture plates with 1.2× 10E6 cells per 2 ml per well in absence of Vinblastine;

(2) Incubate 24 hrs at 37 degrees in humidified incubator (5% CO2);

(3) Aspirate off the spent media and overlay monolayers with 2 ml/well of fresh medium that is 2 uM in Adriamycin (2 uM unlabeled Adriamycin+20000 cpm of 14C-Adr) and the test agent at concentrations varying from 0 to 100 uM;

(4) Following incubation for 3 hours at 37 degrees in humidified incubator, remove media and wash monolayers twice with 2 ml of ice cold buffered saline;

(5) Detach monolayers using 0.5 ml of trypsin/EDTA, collect detached cells and transfer to scintillation vial. Rinse wells once with 0.5 ml of buffered saline and add to same vial containing cells;

(6) Add 5 ml of Beckman Ready-Safe scintillation fluid to vial, vortex and determine radioactivity per sample using a scintillation counter (10 minutes per sample);

(7) For background control: pre-incubate monolayers at 4 degrees for 15 minutes then remove media and add fresh ice-cold media containing Adr (see step 3). Following incubation for 3 hours at 4 degrees remove media and wash monolayers twice with 2 ml ice-cold buffered saline, then proceed as in step 5;

(8) Results are expressed as T/C and ED3x values as defined below:

T/C=pmoles Adr per 10E6 cells treated with test agent/

ED3x=concentration of test agent that produces a 3 fold increase in cellular accumulation of radiolabeled Adr, i.e. T/C=3.

Calculation

Specific cpm=[sample cpm - background cpm]

Specific activity=[cpm/total conc. of Adr]

pmoles Adr = [specific cpm/specific activity]

pmoles Adr per 10E6 cells=[(pmoles Adr per well/number of cells per well)×10E6 cells]

As previously mentioned, compounds of the present invention and salts thereof are useful in potentiating the anticancer effects of chemotherapeutic agents. Such agents can include adriamycin, daunomycin, aclacinomycin A, actinomycin C, actinomycin D, mithramycin, toyomycin, vinblastine, maytansine, bruceantin, homoharintonin, anguindin, neocarcinostatin, mitomycin C and anthramycin.

The compounds of the present invention can be administered with, 24 hours before or up to 72 hours after the administration of the chemotherapeutic agents. When administered with said agents, they can be taken either separately or coadministered in the same formulation.

The compounds of the present invention whether taken separately or in combination with an anti-cancer agent, are generally administered in the form of pharmaceutical compositions comprising at least one of the compounds of formula I and optionally a chemotherapeutic agent, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelation and, for parenteral administration, in the form of injectable solutions of suspensions, and the like.

For use in the potentiation of anticancer agents in a mammal, including man, a compound of formula I is given in an amount of about 0.5–100 mg/kg/day, in single or divided doses. A more preferred dosage range is 2–50mg/kg/day, although in particular cases, at the discretion of the attending physician, doses outside the broader range may be required. The preferred route of administration is generally oral, but parenteral administration (e.g. intramuscular, intravenous, intradermal) will be preferred in special cases, e.g., where oral absorption is impaired as by disease or where the patient is unable to swallow.

The present invention is illustrated by the following examples, but is not limited to the details or scope thereof.

EXAMPLE 1

2,4-Bis-(6,7-dimethoxy-1,2,3,4-tetrahydroisoquinolin-2-yl)- 6-(2-[3,4-dimethoxyphenyl]ethylamino)-1,3,5-triazine phosphate 2-Chloro-4,6-bis-(6,7-dimethoxy-1,2,3,4-tetrahydroisoquinolin- 2-yl)-1,3,5-triazine (1.5 g, 3.01 mM) and 2-(3,4-dimethoxyphenyl)ethylamine (599 mg, 3.30 mM) were stirred in dioxane (15 mL) and sodium hydroxide solution (1M, 5 mL) at reflux for 18 hr. The mixture was cooled, diluted with a saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0.040–0.063 micron, 50 g). Elution of the product with 50% ethyl acetate/hexanes provided 1.85 g of free base. This material was dissolved in hot ethanol and treated with phosphoric acid/ethanol solution (1M, 3.2 mL). Cooling provided a crystalline material, 1.6 g (72%), mp=225°–227° C.

EXAMPLE 2

2,4-Bis-(6,7-dimethoxy-1,2,3,4-tetrahydroisoquinolin-2-yl)-6-(2-[2,3-dimethoxyphenyl)ethylamino)-1,3,5-triazine phosphate 2-Chloro-4,6-bis(6,7-dimethoxy-1,2,3,4-tetrahydroisoquinolin- 2-yl)-1,3,5-triazine (1.32 g, 2.65 mM) and 2-(2,3-dimethoxyphenyl)ethylamine(538 mg, 2.97 mM) were stirred in dioxane (10 mL) and sodium hydroxide solution (1M, 3mL) at reflux for 18 hr. The mixture was cooled and diluted with a saturated sodium chloride solution (50 ml) and extracted with methylene chloride (3×40 mL). Filtration of the separated organic layer through a cotton plug and concentration followed by evaporation from benzene (2×20 mL) provided a foam which was applied as a concentrated methylene chloride solution to a column (25 mm) containing silica gel. Elution of the product with 50% ethyl acetate/hexanes provided 1.42 g of free base. This material (1.17 g) was dissolved in hot ethanol and treated with phosphoric acid/ethanol solution (1M, 2.2 mL). Recrystallization from ethanol/water provided a crystalline material, 1.08 g. (55%), mp=220°–222° C.

EXAMPLE 3

2,4 Bis-(6,7-dimethoxy-1,2,3,4-tetrahydroisoquinolin-2-yl)- 6-(2-phenylethylamino)-1,3,5-triazine phosphate 2-Chloro-4,6-bis-(6,7-dimethoxy-1,2,3,4-tetrahydroisoquinolin- 2-yl)-1,3,5,-triazine (2.0 g, 4.02 mM) and 2-phenylethylamine (509 mg, 4.2 mM) were stirred in dioxane (10 mL) and saturated sodium hydrogen carbonate solution (10 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0.040–0.063 micron, 50 g). Elution of the product with 50% ethyl acetate/hexanes provided 1.25 g of free base. This material was dissolved in hot methylene chloride and treated with phosphoric acid ethanol solution (1M, 2.3 mL). Ethanol was added and boiled until the methylene chloride was removed. Cooling provided a crystalline material, 1.0 g (37%), mp=219°–221° C.

EXAMPLE 4

2,4-Bis-(6,7-dimethoxy-1,2,3,4-tetrahydroisoquinolin-2-yl)-6-( 2-[4-methoxyphenoxy]ethylamino)-1,3,5-triazine phosphate 2-Chloro-4,6-bis-(6,7-dimethoxy-1,2,3,4-tetrahydroisoquinolin- 2-yl)-1,3,5-triazine (1.5 g, 3.01) and 2-(4-methoxyphenoxy)ethylamine(554 mg, 3.31 mM) were stirred in dioxane (15 mL) and sodium hydroxide solution (1M, 5 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0,040–0.063 micron, 50 g). Elution of the product with 40% ethyl acetate/hexanes provided 1.72 g of free base. This material was dissolved in hot methylene chloride and treated with phosphoric acid/ethanol solution (1M, 2.8 mL). Ethanol was added and boiled until the methylene chloride was removed. The solution was saturated with hexanes and cooled to provide a crystalline material, 1.68 g (77%). mp= 193°–194° C.

EXAMPLE 5

2,4-Bis-(6,7-dimethoxy-1,2,3,4-tetrahydroisoquinolin-2-yl)- 6-(benzodioxan-2-ylmethylamino)-1,3,5-triazine phosphate 2-Chloro-4,6-bis-(6,7-dimethoxy-1,2,3,4-tetrahydroisoquinolin- 2-yl)-l,3,5-triazine (1.5 g, 3.01) and 2-(aminomethyl)benzodioxane (994 mg, 6.02 mM) were stirred in dioxane (15mL) and saturated sodium hydrogen carbonate solution (5 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0,040–0.063 micron, 50 g). Elution of the product with 30% ethyl acetate/hexanes provided 1.8 g of free base. This material was dissolved in hot methylene chloride and treated with phosphoric acid/ethanol solution (1M, 2.9 mL). Ethanol was added and boiled until the methylene chloride was removed. Cooling provided a crystalline material 1.30 g(60%), mp=182°–184° C.

EXAMPLE 6

2,4,6-Tris-(6,7-dimethoxy-1,2,3,4-tetrahydroisoquinol-2yl]- 1,3,5-triazine 6,7-Dimethoxy-1,2,3,4-tetrahydroisoquinoline hydrochloride (4.43 g, 18.33 mM) and cyanuric chloride (1.13 g, 6.11 mM) were stirred in dioxane (50 mL) and sodium hydroxide solution (1N, 40 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was crystallized from methylene chloride/ethyl ether, 2.91 g, (73%), mp=166°–169° C.

EXAMPLE 7

2-(6,7-Dimethoxy-1,2,3,4-tetrahydroisoquinolin-2-yl)-4, 6-bis-[2-(3,4-dimethoxyphenyl)ethylamino]-1,3,5-triazine phosphate 2-Chloro-4,6-bis-(2(3,4-dimethoxy)phenylethylamino)-1,3,5-triazine (2.5 g, 5.27 mM) and 6,7-dimethoxy-1,2,3,4-tetrahydroisoquinoline hydrochloride (1.25 g, 5.27 mM) were stirred in dioxane (30 mL) with sodium hydroxide solution (1 N,6 mL) at reflux for 4 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0.040–0.063 micron, 50 g). Elution of the product with 50% ethyl acetate/hexanes provided 2.24 g of free base. This material was dissolved in hot methylene chloride and treated with phosphoric acid/ethanol solution (1M, 3.7 mL). Ethanol was added and boiled until the methylene chloride was partially removed, which caused gelatinous solid to precipitate. Filtration and trituration of the residue ethyl ether and hexanes provided an amorphous solid 1.8 g (47%), mp=179°–181° C.

EXAMPLE 8

2-(6,7-Dimethoxy-1,2,3,4-tetrahydroisoquinolin-2-yl)-4, 6-bis-( 2-methoxy-2-[2,3-dimethoxyphenyl]ethylamino)-1, 3,5-triazine phosphate 2,4-Dichloro-6-(6,7-dimethoxy-1,2,3,4-tetrahydroisoquinolin- 2-yl)-l,3,5-triazine (1.0 g,2.93 mM) and 2-methoxy-2-(2,3-dimethoxyphenyl)ethylamine (1.48 g, 5.98 mM); Rosenmund, Nothnagel, Riesenfeldt, *Chem., Ber.*, 1927, 60, 392–398) were stirred in dioxane (15 mL) and saturated sodium hydrogen carbonate solution (15 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0,040–0.063 micron, 50 g). Elution of the product with 50% ethyl acetate/hexanes provided 980 mg of free base. This material was dissolved in hot ethanol and treated with phosphoric acid/ethanol solution (1M, 1.5 mL). The ethanol was removed in vacuo then dissolved in methylene chloride and ether. Evaporation provided an amorphous material, 990 mg(43%), mp=135°–139° C.

EXAMPLE 9

2-(6,7-Dimethoxy-1,2,3,4-tetrahydroisoquinolin-2-yl)-4, 6-bis-( 2-methoxy-2-[3,4-dimethoxyphenyl]ethylamino)-1, 3,5-triazine phosphate 2,4-Dichloro-6-(6,7-dimethoxy-1,2,3,4-tetrahydroisoquinolin- 2-yl)-l,3,5-triazine (328 mg, 0.96 mM) and 2-methoxy-2-(3,4-dimethoxyphenyl) ethylamine(0.5 g, 2.02 mM; Rosenmund, Nothnagel, Riesenfeldt *Chem. Ber.*, 1927, 60, 392–398) were stirred in dioxane (15 mL) with saturated sodium hydrogen carbonate solution (15 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0,040–0,063 micron, 50 g). Elution of the product with 50 % ethyl acetate/hexanes provided 370 mg of free base. The material was dissolved in hot ethanol and treated with phosphoric acid/ethanol solution (1M, 0.6 mL). The solution was saturated with hexanes and allowed to cool to provide prisms, 185 mg(24%), mp=132°–140° C.

EXAMPLE 10

2-(6,7-Dimethoxy-1-[3,4-dimethoxybenzyl]-1,2,3,4-tetrahydroisoquinolin- 2-yl)-4-(6,7-dimethoxy-1,2,3,4-tetrahydroisoquinolin- 2-yl)-6-amino-1,3,5-triazine hydrobromide 2-Chloro-4(6,7-dimethoxy-1,2,3,4-tetrahydroisoquinolin-2-yl)-6-amino-1,3,5-triazine (2.0 g, 6.22) and 1,2,3,4-tetrahydropapaverine hydrochloride (2.6 g, 6.22 mM) were stirred in dioxane (12 mL) with sodium hydroxide solution (1N, 13 mL) at reflux for 18 hr. The mixture was cooled and diluted with saturated sodium chloride solution and extracted with methylene chloride (3×40 mL). Filtration through a cotton plug and concentration followed by evaporation from benzene (2×20 mL) provided a foam which was applied as a concentrated methylene chloride solution to a column (35 mm) containing silica gel (0.040–0.063 micron, 100 g). Elution of the product with 50% ethyl acetate/hexanes provided 3.28 g of free base. Conversion to the hydrobromide salt with 2N hydrobromic acid/methanol, evaporation to a solid and recrystallization from ethanol/hexanes provided an amorphous solid 2.46 g (56%), mp=150° C.

EXAMPLE 11

2-(6,7-Dimethoxy-1,2,3,4-tetrahydroisoquinolin-2-yl)-4-( 3,3-diphenylpropylamino)-6-amino-1,3,5-triazine phosphate 2-Chloro-4-(6,7-dimethoxy-1,2,3,4-tetrahydro-isoquinolin- 2-yl)-6-amino-1,3,5-triazine (2.0 g, 6.22) and 3,3-diphenylpropylamine (1.35 g, 6.22 mM) were stirred in dioxane (12 mL) with sodium hydroxide solution (1N, 13 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (35 mm) containing silica gel (0.040–0,063 micron, 100 g). Elution of the product with 50% ethyl acetate/hexanes provided 2.9 g of free base. This material was dissolved in hot ethanol and treated with phosphoric acid/ethanol solution (1M, 5.8 mL). Upon cooling white crystals formed, 2.8 g (76%), mp=235°–237° C. (dec).

EXAMPLE 12

2,4-Bis-(6,7-dimethoxy-1,2,3,4-tetrahydroisoquinolin-2-yl]- 6-amino-1,3,5-triazine hydrochloride 2,4-Dichloro-6-amino-1,3,5-triazine (5.13 g, 31.1 mM) and 6,7-dimethoxy-1,2,3,4-tetrahydroisoquinoline hydrochloride (14.72 g, 64 mM) were stirred in dioxane (40 mL) with sodium carbonate solution (2N, 65 mL) at reflux for 3 hr. The mixture was cooled and diluted with saturated sodium chloride solution (1000 mL) and extracted with methylene chloride (3×75 mL). Filtration through a cotton plug and concentration followed by evaporation from benzene (2×20 mL) provided a foam, 16.5 g. This material was combined with 7.8 g of crude product prepared analogously and recrystallized from chloroform/methanol to provide 13.85 g(61%). Recrystallization of free base (2.6 g) from hydrochloric acid/methanol (1N) provided a yellow powder, 2.17 g(78%), mp= 259°–261° C.

EXAMPLE 13

2-(6,7-Dimethoxy-1-[3,4-dimethoxybenzyl]-1,2,3,4-tetrahydroisoquinolin- 2-yl)-4,6-bis-(2-[3,4-dimethoxyphenyl] ethylamino)- 1,3,5-triazine phosphate 2-Chloro-4,6-bis-(2-(3,4-dimethoxyphenyl)ethylamino)-1,3,5-triazine (500 mg, 1.06 mM) and 1,2,3,4-tetrahydropapaverine hydrochloride (380 g, 1.06 mM) were stirred in dioxane (6 mL) with sodium hydroxide solution (1N, 3.5 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0.040–0.063 micron, 50 g). Elution of the product with ethyl acetate provided 634 mg of free base. This material was dissolved in hot methylene chloride and treated with phosphoric acid/ethanol solution (1M, 1 mL). Ethanol was added and boiled until the methylene chloride was removed. Cooling provided an electrostatic powder, 505 mg(54%), mp=188°–190.5° C.

EXAMPLE 14

2,4-Bis-(6,7-dimethoxy-1,2,3,4-tetrahydroisoquinolin-2-yl)- 6-(N-methyl-N-benzylamino)-1,3,5-triazine 2-Chloro-4,6-bis-(6,7-dimethoxy-1,2,3,4-tetrahydroisoquinolin- 2-yl)-1,3,5-triazine (1.5 g, 3.01 mM) and N-methyl-N-benzylamine (365 mg, 3.0 mM) were stirred in dioxane (15 mL) with sodium hydroxide solution (1M, 5 mL) at reflux for 21 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0.040–0.063 micron, 50 g). Elution of the product with 35% ethyl acetate/hexanes provided 1.69 g of free base (96%). This material was dissolved in hot methylene chloride. Ethanol was added and boiled until the methylene chloride was removed. The solution was saturated with hexanes and cooled to provide a crystalline material, 1.02 g(58%), mp=151°–152° C.

EXAMPLE 15

2,4,6-Tris-(2-[3,4-dimethoxyphenyl]ethylamino)-1,3,5-triazine 2-(3,4-Dimethoxyphenyl)ethylamine (1.4 g, 7.7 mM) and cyanuric chloride (461 mg, 2.5 mM) were stirred in dioxane (10 mL) with sodium hydroxide solution (1N, 5 mL) at reflux for 18 hr. The mixture was cooled and diluted with saturated sodium chloride solution (50 mL) and extracted with methylene chloride (3×40 mL). Filtration through a cotton plug and concentration followed by evaporation from benzene (2×20 mL) provided a foam which was applied as a concentrated methylene chloride solution to a column (25 mm) containing silica gel (0.040–0.063 micron, 50 g). Elution of the product with ethyl acetate provided 832 mg of free base (54%). This material was dissolved in hot methylene chloride and treated with phosphoric acid/ethanol solution (1M, 1.36 mL). Ethanol was added and boiled until the methylene chloride was removed. The saturated solution was cooled to provide a crystalline material, 720 mg (40%), mp=157.5°–159° C.

EXAMPLE 16

Starting with 2-chloro-4-(6,7-dimethoxy-1,2,3,4-tetrahydroisoquinolin- 2-yl)-6-(2-[3,4-dimethoxyphenyl]ethylamino)- 1,3,5-triazine and the appropriate amine and employing the procedure of Example 1 the following compounds were prepared as the phosphate salt:

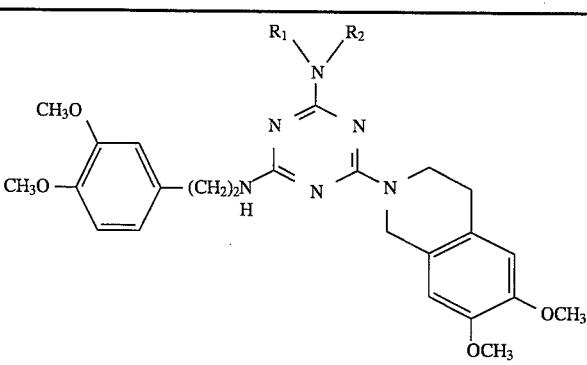

| $R_1$ | $R_2$ | m.p., °C. |
|---|---|---|
| 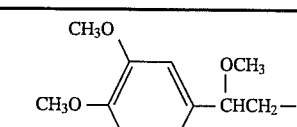 | H | 182–184 |
| 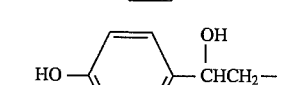 | H | 192–194 |
| 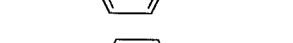 | H | 211–212 |

EXAMPLE 17

Starting with 2-chloro-4-(6,7-dimethoxy-1-[3,4-dimethoxybenzyl]-1,2,3,4-tetrahydroisoquinolin-2-yl)-6-(2-[3,4-dimethoxyphenyl]ethylamino)-1,3,5-triazine and the appropriate amine and employing the procedure of Example 1, the following compounds were prepared as the phosphate salt:

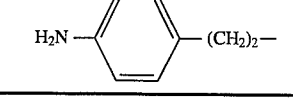

| $R_1$ | $R_2$ | m.p., °C. |
|---|---|---|
| 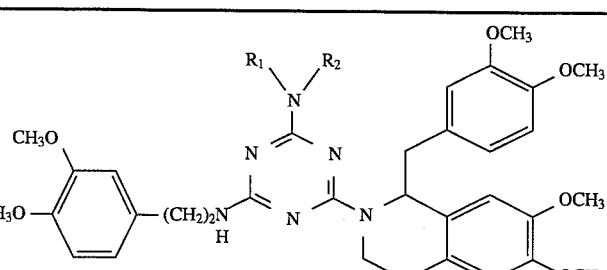 | H | 131–148 |
| 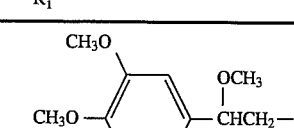 | H | 134–135 |

PREPARATION A

2-Amino-4,6-dichloro-1,3,5-triazine

A stirred suspension of cyanuric chloride (3.7 g, 30 mM) in water (25 mL) was treated with NH$_4$OH (2.42 mL of a 28% solution diluted to 7.5 mL) at 0° C. Stirring was continued for 1 hr at 0° C. and 0.5 hr at 10° C. The product was filtered and rinsed with water until the filtrates were neutral. Drying (60° C., 0.2 mm) provided 2.84 g, (86%), mp=234°–235° C.

PREPARATION B

2-Chloro-4,6-bis-(6,7-dimethoxy-1,2,3,4-tetrahydroisoquinolin- 2-yl)-1,3,5 triazine A vigorously stirred dispersion of 6,7-dimethoxy- 1,2,3, 4-tetrahydroisoquinoline (9.57 g, 40.4 mM) and cyanuric chloride (3.75 g, 20.2 mM) in dioxane (80 mL) was treated with sodium carbonate solution (0° C., 1M, 80 mL) at 0° C. for 0.5 hr then 4 hr at ambient temperature. Extraction with chloroform (4×70 mL), washing with saturated sodium chloride solution (80 mL), filtration through a cotton plug and concentration afforded an oil. Evaporation from benzene (2×40 mL) left a white foam which was triturated with hot methanol to provide a white crystalline solid, 9.35 g, (94%), mp=149°–151° C.

PREPARATION C

2-Chloro-4,6-bis (2-[3,4-dimethoxyphenyl]ethylamino)- 1,3,5-triazine

Cyanuric chloride (2.0 g, 10.85 mM) was dispersed in dioxane (80 mL) with stirring and 2-(3,4-dimethoxyphenyl)ethylamine (3.93 g, 21.68 mM) was introduced dropwise over 2 minutes. Sodium hydroxide (1N, 24 mL) was added dropwise over 5 minutes then the whole was brought to reflux for 18 hours. Cooling to ambient temperature caused a white solid to precipitate. Diethyl ether (100 mL) was introduced to fully precipitate the product which was filtered, rinsed with diethyl ether and dried. 5.05 g, (98%), mp=186°–186.5° C.

PREPARATION D

2-Chloro-4-(6,7-dimethoxy-1,2,3,4-tetrahydroisoquinolin-2-yl)- 6-amino-1,3,5-triazine 2-amino-4,6-dichloro-1,3,5-triazine (9.7 g, 58.8 mM) was dispersed in water (50 mL), sodium carbonate solution (2N, 60 mL) and dioxane 15 mL) at 0° C. 6,7-dimethoxy-1,2,3,4-tetrahydroisoquinoline hydrochloride (13.9 g, 58.8 mM) was added and the mixture was stirred vigorously for 1 hr. The product was filtered, rinsed with water, dried and recrystallized from methanol; 14.3 g (75%), mp=196°–197° C.

PREPARATION E 2,4-Dichloro-6-(6,7-dimethoxy-1,2,3,4-tetrahydro-isoquinolin- 2-yl)-1,3,5-triazine To a 0° C. stirred slurry of cyanuric chloride (8.03 g, 43.5 mM) in saturated sodium hydrogen carbonate solution (300 mL) was added 6,7-dimethoxy-1,2,3,4-tetrahydro-isoquinoline hydrochloride (10 g, 43.5 mM) in water (50 mL) at a rate that maintained the internal temperature below 8° C. After 10 min the product was extracted with methylene chloride, filtered through a cotton plug and concentrated to a solid. Filtration of a concentrated methylene chloride solution of the crude product through a 2×2 inch silica gel pad eluting with 50% ethyl acetate/hexanes provided pure product, 12.3 g, (83%).

PREPARATION F

2-Chloro-4-(6,7-dimethoxy-1-[3,4-dimethoxybenzyl]-1, 2,3,4-tetrahydroisoquinolin- 2-yl)-6-amino-1,3,5-triazine 2-amino-4,6-dichloro-1,3,5-triazine (696 mg, 4.2 mM) and 1,2,3,4-tetrahydropapervine hydrochloride (2.0 g, 4.2 mM) were combined and stirred vigorously in saturated sodium hydrogen carbonate solution and dioxane (25 mL each) for 2.5 hr at ambient temperature. The mixture was diluted with saturated sodium chloride solution (50 mL) and extracted with methylene chloride (3×40 mL). Filtration through a cotton plug and concentration provided a 2.35 g, (100%), of white powder.

PREPARATION G

2-Chloro-4-(6,7-dimethoxy-1,2,3,4-tetrahydroisoquinolin-2-yl)- 6-(2-[3,4-dimethoxyphenyl]ethylamino)-1,3,5-triazine 2,4-Dichloro-6-(6,7-dimethoxy-1,2,3,4-tetrahydroisoquinolin- 2-yl)-1,3,5-triazine (3.08 g, 9.03 mM) in dioxane (50 mL) and aqueous sodium carbonate solution (50 mL, 10% solution) was treated with 2-(3,4-dimethoxyphenyl)ethylamine (1.64 g, 9.03 mM). After stirring 18 hrs at ambient temperature the mixture was extracted with methylene chloride (3×75 mL). Filtration through a cotton plug and concentration provided a solid which was recrystallized from methylene chloride/ethanol to provide 3.52 g, (80%), mp=152°–153° C.

PREPARATION H

2-Chloro-4-(6,7-dimethoxy-1-[3,4-dimethoxybenzyl]-1,2, 3,4-tetrahydroisoquinolin- 2-yl)-6-(2-[3,4-dimethoxyphenyl]ethylamino)-1,3,5-triazine cyanuric chlorine (4.86 g, 26.4 mM) and tetrahydro-papervine hydrochloride (10 g, 26.4 mM) were combined and stirred vigorously in saturated sodium hydrogen carbonate solution (150 mL) and dioxane (25 mL each) for 0.5 hr at 0°–5° C. The mixture was extracted with methylene chloride (3×100 mL). Filtration through a cotton plug and concentration provided white solids which were vigorously stirred in dioxane (50 mL) and treated with 2-(3,4-dimethoxyphenyl)ethylamine (4.78 g, 9.03 mM). To this thick mixture was added 15% sodium carbonate solution (150 mL) and the resulting mixture was stirred 3 hr at room temperature at which time product was filtered and rinsed with ether (3×50 mL).

Recrystallization of the solids from methylene chloride/ ethanol provided 15.4 g, (combined from three crops, 92%), mp=134°–135° C.

We claim:

1. A compound of the formula

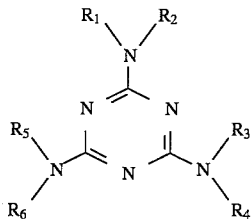

I and the pharmaceutically acceptable acid addition salts thereof, wherein $R_1$ and $R_2$ are taken together with the nitrogen to which they are attached and are of the formula

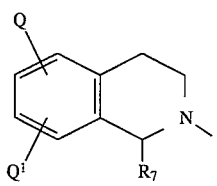

wherein $R_7$ is hydrogen, alkyl having one to three carbon atoms or dialkoxyphenylalkyl said alkoxy each having from one to three carbon atoms and said alkyl having one to three carbon atoms, Q and $Q^1$ are each hydrogen, alkyl having one to three carbon atoms, alkoxy having one to three carbon atoms, fluoro, chloro, bromo, iodo, trifluoromethyl, amino, alkylamino having one to three carbon atoms or dialkylamino having two to six carbon atoms or Q and $Q^1$ taken together are methylenedioxy or ethylenedioxy; $R_3$ is hydrogen or alkyl having one to three carbon atoms; $R_4$ is (a) hydrogen, (b) alkyl having one to three carbon atoms, (c) aralkyl of the formula

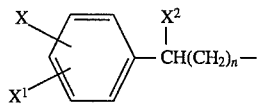

wherein X and $X^1$ are each hydrogen, alkyl having one to three carbon atoms, hydroxy, alkoxy having one to three carbon atoms, fluoro, chloro, bromo, iodo, trifluoromethyl, amino, alkylamino having one to three carbon atoms or dialkylamino having two to six carbon atoms, or X and $X^1$ taken together are methylenedioxy or ethylenedioxy, n is an integer of 0 or 1 and $X^2$ is hydrogen, alkoxy having one to three carbon atoms or hydroxy or (d) aralkyl of the formula

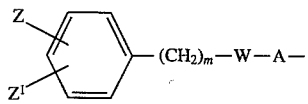

wherein Z and $Z^1$ are each hydrogen, alkyl having one to three carbon atoms, hydroxy, alkoxy having one to three carbon atoms, fluoro, chloro, bromo, iodo, trifluoromethyl, amino, alkylamino having one to three carbon atoms or dialkylamino having two to six carbon atoms, or Z and $Z^1$ taken together are methylenedioxy or ethylenedioxy; m is an integer of 0 or 1, W is O, S or a chemical bond and A is alkylene having two to four carbon atoms, provided that when m is O and W is a chemical bond then A cannot be ethylene or $R_3$ and $R_4$ when taken together with the nitrogen to which they are attached are of the formula

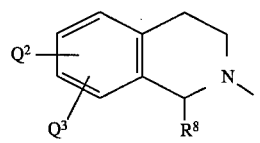

wherein $Q^2$ and $Q^3$ are each hydrogen, alkyl having one to three carbon atoms, alkoxy having one to three carbon atoms, fluoro, bromo, iodo, chloro, trifluoromethyl, amino, alkylamino having one to three carbon atoms or dialkylamino having two to six carbon atoms or $Q^2$ and $Q^3$ taken together are methylenedioxy or ethylenedioxy and $R_8$ is hydrogen, alkyl having one to three carbon atoms or dialkoxyphenylalkyl said alkoxy each having from one to three carbon atoms and said alkyl having from one to three carbon atoms; $R_5$ is (a) hydrogen, (b) alkyl having one to three carbon atoms, (c) benzodioxan-2-ylmethyl, (d) aralkyl of the formula

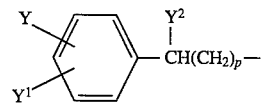

wherein Y and $Y^1$ are each hydrogen, alkyl having one to three carbon atoms, hydroxy, alkoxy having one to three carbon atoms, fluoro, chloro, bromo, iodo, trifluoromethyl, amino, alkylamino having one to three carbon atoms or dialkylamino having two to six carbon atoms, or Y and $Y^1$ taken together are methylenedioxy or ethylenedioxy, p is an integer of 0 or 1 and $Y^2$ is hydrogen, hydroxy or alkoxy having one to three carbon atoms or (e) aralkyl of the formula

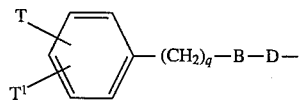

wherein T and $T^1$ are each hydrogen, alkyl having one to three carbon atoms, hydroxy, alkoxy having one to three carbon atoms, fluoro, chloro, bromo, iodo, trifluoromethyl, amino, alkylamino having one to three carbon atoms or dialkylamino having two to six carbon atoms, or T and $T^1$ taken together are methylenedioxy or ethylenedioxy, q is an integer of 0 or 1, B is O, S or a chemical bond and D is alkylene having two to four carbon atoms provided that when q is 0 and B is a chemical bond then D cannot be ethylene; $R_6$ is hydrogen or alkyl having one to three carbon atoms or $R_5$ and $R_6$ when taken together with the nitrogen to which they are attached form a moiety of the formula

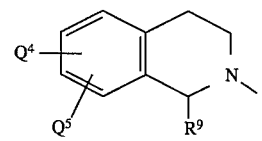

wherein $Q^4$ and $Q^5$ are each hydrogen, alkyl having one to three carbon atoms, alkoxy having one to three carbon atoms, fluoro, bromo, iodo, chloro, trifluoromethyl, amino, alkylamino having one to three carbon atoms or dialkylamino having two to six carbon atoms, or $Q^4$ and $Q^5$ taken together are methylenedioxy or ethylenedioxy and $R_9$ is hydrogen, alkyl having one to three carbon atoms or dialkoxyphenylalkyl said alkoxy having one to three carbon atoms and said alkyl having one to three carbon atoms, with the proviso that when $X^2$ is hydroxy or said alkoxy then n is 1 and when $Y^2$ is hydroxy or said alkoxy then p is 1.

2. A compound of claim 1, wherein $R_1$ and $R_2$ are taken together with the nitrogen atom to which they are attached and form a moiety of the formula

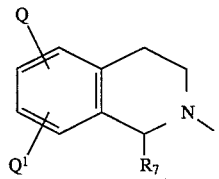

wherein Q is 6-methoxy, $Q^1$ is 7-methoxy and $R_7$ is hydrogen or dialkoxyphenylalkyl, said alkoxy each having one to three carbon atoms and said alkyl having from one to three carbon atoms; $R_3$ and $R_4$ when taken together with the nitrogen atom to which they are attached form a moiety of the formula

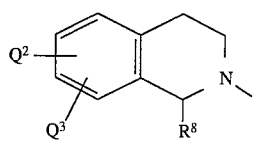

wherein $Q^2$ is 6-methoxy, $Q^3$ is 7-methoxy and $R_8$ is hydrogen; and $R_5$ is hydrogen, benzodioxan-2-yl or aralkyl of the formula

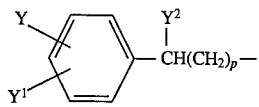

wherein Y and $Y^1$ are each alkoxy having one to three carbon atoms, $Y^2$ is hydrogen and p is 1.

3. The compound of claim 2, wherein $R_7$ is hydrogen, $R_5$ is aralkyl of the formula

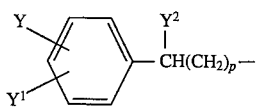

Y is 3-methoxy, $Y^1$ is 4-methoxy and $R_6$ is hydrogen.

4. The compound of claim 2, wherein $R_7$ is 3,4-dimethoxybenzyl, $R_5$ is benzodioxan-2-yl and $R_6$ is hydrogen.

5. The compound of claim 2, wherein $R_7$ is 3,4-dimethoxybenzyl and $R_5$ and $R_6$ are each hydrogen.

6. A compound of claim 1, wherein $R_1$ and $R_2$ when taken together with the nitrogen atom to which they are attached form a moiety of the formula

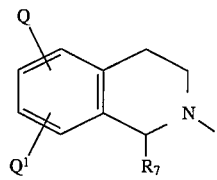

wherein Q is 6-methoxy, $Q^1$ is 7-methoxy and $R_7$ is hydrogen or dialkoxyphenylalkyl said alkoxy each having one to three carbon atoms and said alkyl having one to three carbon atoms; $R_3$ is hydrogen, $R_4$ is aralkyl of the formula

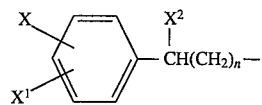

wherein n is an integer of 1; $R_5$ is aralkyl of the formula

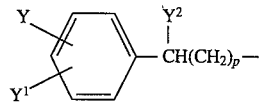

wherein p is an integer of 1 and $Y^2$ is hydrogen and $R_6$ is hydrogen.

7. The compound of the claim 6, where $R_7$ is hydrogen, X is 3-methoxy, $X^1$ is 4-methoxy, $X^2$ is hydrogen, Y, is 3-methoxy and $Y^1$ is 4-methoxy.

8. The compound of claim 6, where $R_7$ is 3,4-dimethoxybenzyl, X is 3-methoxy, $X^1$ is 4-methoxy, $X^2$ is hydrogen, Y is 3-methoxy and $Y^1$ is 4-methoxy.

9. The compound of claim 6, where $R_7$ is hydrogen, X is 3-methoxy, $X^1$ is 4-methoxy, $X^2$ is methoxy Y is 3-methoxy $Y^1$ is 4-methoxy.

10. The compound of claim 6, where $R_7$ is hydrogen, X is hydrogen, $X^1$ is 4-amino $X^2$ is hydrogen, Y is 3-methoxy and $Y^1$ is 4-methoxy.

11. The compound of claim 6, where $R_7$ is 3,4-dimethoxybenzyl, X is 3-methoxy, $X^1$ is 4-methoxy, $X^2$ is methoxy, Y is 3-methoxy and $Y^1$ is 4-methoxy.

12. The compound of claim 6, where $R_7$ is 3,4-dimethoxybenzyl, X is hydrogen, $X^1$ is 4-amino, Y is 3-methoxy and $Y^1$ is 4-methoxy.

13. A method of inhibiting a P-glycoprotein in a mammal in need of such treatment which comprises administering to said mammal a P-glycoprotein inhibiting amount of a compound according to claim 1.

14. A pharmaceutical composition for administration to a mammal which comprises a p-glycoprotein inhibiting amount of a compound of claim 1, a pharmaceutically acceptable carrier.

* * * * *